United States Patent
Harrison et al.

(10) Patent No.: US 7,526,096 B2
(45) Date of Patent: *Apr. 28, 2009

(54) IN THE EAR AUXILIARY MICROPHONE FOR BEHIND THE EAR HEARING PROSTHETIC

(75) Inventors: William Vanbrooks Harrison, Valencia, CA (US); Lee F Hartley, Calgary (CA); Philip A Segel, Englewood, CO (US); Scott Crawford, Castaic, CA (US); C. Geoffrey E Fernald, La Canada, CA (US)

(73) Assignee: Advanced Bionics, LLC, Valencia, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 11/530,869

(22) Filed: Sep. 11, 2006

(65) Prior Publication Data

US 2007/0003089 A1    Jan. 4, 2007

Related U.S. Application Data

(62) Division of application No. 10/823,962, filed on Apr. 14, 2004, now Pat. No. 7,106,873, which is a division of application No. 09/927,130, filed on Aug. 10, 2001, now Pat. No. 6,775,389.

(30) Foreign Application Priority Data

Aug. 8, 2002    (WO) ............... PCT/US02/025311

(51) Int. Cl.
*H04R 25/00*    (2006.01)

(52) U.S. Cl. ............... 381/330; 381/326; 381/328

(58) Field of Classification Search .......... 381/312, 381/322, 326, 327, 328, 330, 380, 381, 71.6, 381/374, 375; 607/56, 57; 600/25; 379/52, 379/430; 128/903

See application file for complete search history.

(56) References Cited

U.S. PATENT DOCUMENTS

| 2,930,856 A | 3/1960 | Toht |
| 3,098,127 A | 7/1963 | Huth |
| 3,396,245 A | 8/1968 | Flygstad |
| 4,291,203 A | 9/1981 | Bellafiore |

(Continued)

FOREIGN PATENT DOCUMENTS

DE    3502178 A1    8/1985

(Continued)

*Primary Examiner*—Huyen D Le
(74) *Attorney, Agent, or Firm*—Mary Elizabeth Bush; Victoria A Poissant; Bryant R. Gold

(57) ABSTRACT

An In The Ear (ITE) microphone which converts audio sounds into electrical signals which are then processed by a speech processor to generate electrical pulses to stimulate nerves in the cochlea, improves the acoustic response of a Behind The Ear (BTE) Implantable Cochlear Stimulation (ICS) system during telephone use. An acoustic seal provided by holding a telephone earpiece against the ear provides improved coupling of low frequency (up to about 1 KHz) sound waves, sufficient to overcome losses due to the near field acoustic characteristics common to telephones. In an exemplary embodiment, the ITE microphone is connected to a removable ear hook of the BTE ICS system by a short bendable stalk.

20 Claims, 4 Drawing Sheets

U.S. PATENT DOCUMENTS

| | | | |
|---|---|---|---|
| 4,696,287 A | | 9/1987 | Hortmann et al. |
| 4,727,582 A | | 2/1988 | de Vries et al. |
| 5,086,464 A | * | 2/1992 | Groppe ........................ 381/331 |
| 5,369,857 A | | 12/1994 | Sacherman et al. |
| 5,535,282 A | | 7/1996 | Luca |
| 5,701,348 A | | 12/1997 | Shennib et al. |
| 5,757,933 A | | 5/1998 | Preves et al. |
| 5,782,744 A | | 7/1998 | Money |
| 5,790,672 A | | 8/1998 | Klostermeier |
| 5,814,095 A | | 9/1998 | Muller et al. |
| 5,824,022 A | * | 10/1998 | Zilberman et al. ............ 607/57 |
| 5,906,635 A | | 5/1999 | Maniglia |
| 6,161,046 A | | 12/2000 | Maniglia et al. |
| 6,216,040 B1 | | 4/2001 | Harrison |
| 6,259,951 B1 | | 7/2001 | Kuzma et al. |
| 6,272,382 B1 | | 8/2001 | Faltys et al. |
| 6,308,101 B1 | | 10/2001 | Faltys et al. |
| 6,748,094 B1 | | 6/2004 | Tziviskos et al. |

FOREIGN PATENT DOCUMENTS

| | | |
|---|---|---|
| WO | 01/56521 A1 | 8/2001 |
| WO | 03/015470 A2 | 2/2003 |
| WO | 03/015470 A3 | 2/2003 |

* cited by examiner

IN THE EAR AUXILIARY MICROPHONE FOR BEHIND THE EAR HEARING PROSTHETIC

The present application is a Divisional of U.S. application Ser. No. 10/823,962, filed Apr. 14, 2004, to be issued as U.S. Pat. No. 7,106,873 on Sep. 12, 2006; which is a Divisional of U.S. application Ser. No. 09/927,130, filed Aug. 10, 2001, issued as U.S. Pat. No. 6,775,389; and is related to U.S. application Ser. No. 10/731,049, filed Dec. 9, 2003, issued as U.S. Pat. No. 7,003,876; which applications and patents are incorporated herein by reference in their entireties.

BACKGROUND OF THE INVENTION

The present invention relates to hearing devices for aiding the hearing impaired and the profoundly deaf, and more particularly to an In The Ear (ITE) auxiliary microphone connected to a Behind The Ear (BTE) speech processor through a removable ear hook. The microphone of the present invention is especially useful for a user conversing over a telephone.

Implantable Cochlear Stimulation (ICS) systems are known in the art. Such systems are used to help the profoundly deaf (those whose middle and/or outer ear is dysfunctional, but whose auditory nerve remains intact) to hear. The sensation of hearing is achieved by directly exciting the auditory nerve with controlled impulses of electrical current, which impulses are generated as a function of perceived audio sounds. The audio sounds are picked up by a microphone carried externally (not implanted) by the deaf person and converted to electrical signals. The electrical signals, in turn, are processed and conditioned by a Wearable Signal Receiver and Processor (WP) in an appropriate manner, e.g., converted to a sequence of pulses of varying width and/or amplitude, and then transmitted to an implanted receiver circuit of the ICS system. The implanted receiver circuit generates electrical current as a function of the processed signal it receives from the WP (which in turn is based on the audio sounds picked up by the external microphone). The implanted receiver circuit is connected to an implantable electrode array that has been implanted into the cochlea of the inner ear. The electrical current generated by the implanted receiver circuit is applied to individual electrode pairs of the electrode array. It is this electrical current which directly stimulates the auditory nerve and provides the user with the sensation of hearing.

While known ICS systems have succeeded in providing hearing to the deaf, ICS systems also have the disadvantage of appearing unsightly. ICS systems include an external headpiece, positioned on the side of the user's head, and require an external cable running from the external headpiece to the WP. The WP is typically worn or carried by the user on a belt or in a pocket. While the WP is not too large, it is likewise not extremely small, and hence also represents an inconvenience for the user. The cable which connects the WP with the headpiece is particularly a source of irritation and self-consciousness for the user.

The above-described aesthetic considerations and inconvenience of an external wire are addressed by U.S. Pat. No. 5,824,022, issued Oct. 20, 1998, for "Cochlear Stimulation System Employing Behind-The-Ear (BTE) Speech Processor With Remote Control." The '022 patent teaches a small single external device that performs the functions of both the WP and the headpiece. The external device is positioned behind the ear to minimize its visibility, and requires no cabling to additional components. The '022 patent is incorporated herein by reference.

While the BTE device taught by the '022 patent resolves the issues of aesthetics and inconvenience, the placement of the microphone in the BTE device case results in poor microphone performance when using a telephone. The near field acoustic characteristics of known telephones, and the absence of a seal between the telephone earpiece and the microphone in the BTE case, degrades the coupling of low frequency information up to about 1 KHz. Further, known ICS systems and hearing aids use a telecoil residing near the earpiece of a telephone handset to detect the magnetic field produced by the speaker in the handset, however, low magnetic field phones and cell phones using piezo transducers, do not couple well with telecoils.

Therefore, there is a need to improve the performance of known ICS systems when the user is conversing over a telephone.

SUMMARY OF THE INVENTION

The present invention addresses the above and other needs by providing an In The Ear (ITE) microphone that improves the acoustic response of a Behind The Ear (BTE) Implantable Cochlear Stimulation (ICS) system during telephone use. An acoustic seal provided by holding a telephone earpiece against the outer ear provides improved coupling of low frequency (up to about 1 KHz) sound waves, sufficient to overcome losses due to the near field acoustic characteristics resulting from the telephone microphone cooperation. In a preferred embodiment, the ITE microphone is connected to a removable ear hook of the BTE ICS system by a short bendable stalk.

In accordance with one aspect of the invention, there is provided an ITE microphone for a BTE ICS system, which microphone is placed within the concha of the ear. When a telephone handset is held against the ear, the phone seals against the outer ear, creating a chamber wherein the microphone resides. Sealing the microphone within such chamber results in improved frequency fidelity due to the sealing in of the sound pressure. Such sealing also reduces the amount of outside noise that reaches the microphone. Advantageously, the BTE ICS system does not require any earmolding to provide adequate sealing. Further, the positioning of the microphone within the ear improves hearing by using the natural acoustics of the ear.

It is a further feature of the invention to provide a BTE ICS system that works equally well with low magnetic field phones and cell phones using piezo transducers which do not couple well to a telecoil. The ITE microphone relies entirely on the acoustic signal transmitted by the speaker in the telephone handset, which speaker is designed to achieve the acoustic performance objectives of the unaided hearing population. The performance of the BTE ICS system using the ITE microphone is therefore unaffected by the type of speaker (or sound transducer) used in the telephone handset.

It is an additional feature of the present invention, that when exercised in conjunction with an ICS system, there is no acoustic feedback from a microphone to affect performance. Conventional hearing aids use a speaker in the user's ear to broadcast an amplified acoustic signal to the user. If an ITE microphone was used in the same ear, the result would be severe acoustic feedback. The present invention is applied to ICS systems, wherein the output of the ICS system is electrical stimulation of the cochlea, not an acoustic signal.

It is a further additional feature that use of the ITE microphone does not result in chafing to the skin of the ear. The ITE microphone of the present invention includes a bendable stalk, which stalk retains a shape once the stalk is bent into that shape. The stalk may thus be bent to avoid rubbing against the skin of the ear, and the resulting chafing of the skin.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
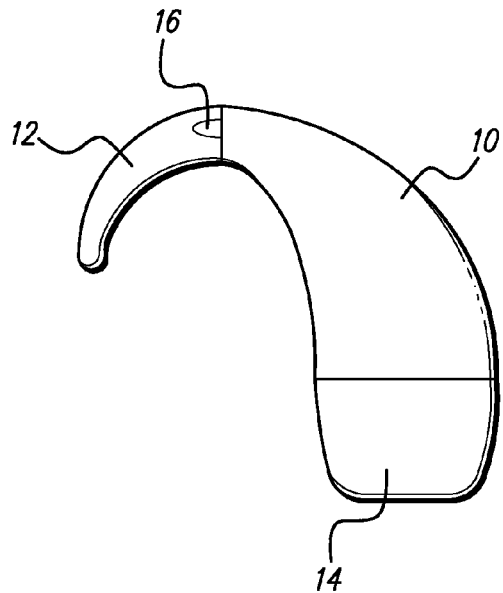
FIG. 1A depicts a prior art BTE device and earhook.
Figure 1B:
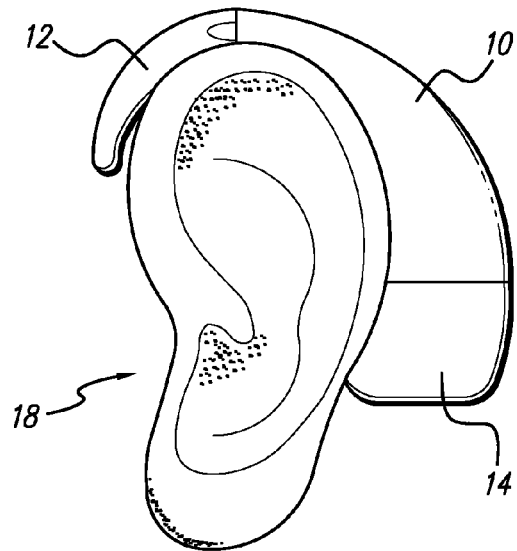
FIG. 1B depicts the prior art BTE device and earhook placed upon the ear of a user.

The In The Ear (ITE) microphone of the present invention improves the acoustic response of a Behind The Ear (BTE) Implantable Cochlear Stimulation (ICS) system during telephone use. As shown in FIG. 1A, when combined (or connected together), a prior art earhook 12 and BTE device 10 of an ICS system resemble a common BTE hearing aid. The earhook 12 is arched and hooks in front of the ear. The BTE device 10 continues the arch to the rear of the ear and is positioned behind the ear. A battery compartment 14 is removably attached to the bottom of the BTE device 10. Various batteries of different sizes may be interchangeably attached to the BTE device 10 depending upon the needs of a user. A more detailed description of a BTE device may be found in U.S. Pat. No. 5,824,022, previously incorporated herein by reference. In known BTE devices 10, a BTE microphone is positioned in the case of the BTE device 10 behind a microphone port 16. The earhook 12 typically defines a recess cooperating with the port 16 to facilitate the communication of sound waves with the BTE microphone. The BTE device 10 with the earhook 12 attached, is shown residing on an ear 18 in FIG. 1B.

Figure 1C:
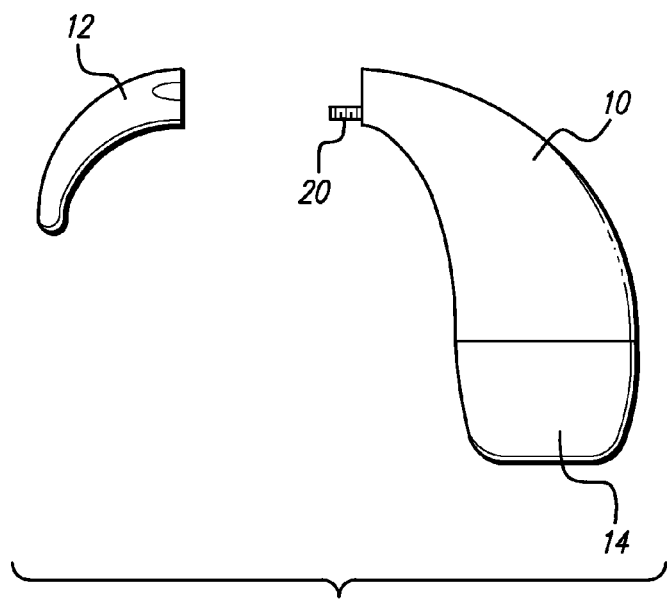
FIG. 1C shows the prior art BTE device and earhook with the earhook detached from the BTE device.

Turning to FIG. 1C, a coaxial connector 20 is shown attached to the BTE device 10. Such co-axial connector 20 is disclosed in currently pending U.S. patent application Ser. No. 09/785,629 filed Feb. 16, 2001 for "Connector System for BTE Hearing Devices." The coaxial connector 20 serves as both an attaching fixture for the standard earhook 12 and special earhooks (i.e., provides a mechanical connection), and as an electrical connector for auxiliary devices (i.e., provides an electrical connection between the BTE electronics circuits and other electronic devices or sensors included within, or attached to, an earhook). Advantageously, the dual use feature of the coaxial connector 20 eliminates the need to provide a separate connector for connecting (electrically or mechanically) auxiliary devices to the BTE device 10. The '629 application teaches the construction and use of the coaxial connector to mechanically and electrically connect a special earhook to a BTE device 10. The '629 application also discloses several special earhooks intended to add features to the BTE ICS device. The '629 application does not however contemplate a special earhook which provides an ITE microphone. The '629 application is herein incorporated by reference.

Figure 2:
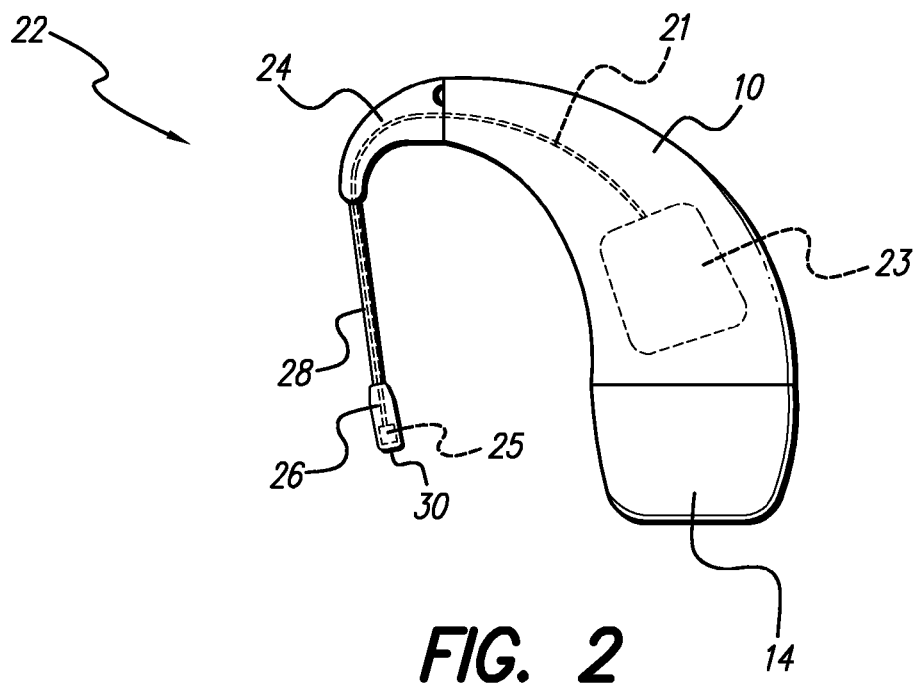
FIG. 2 shows the BTE device with the In The Ear (ITE) microphone attached.

An ITE microphone earhook 22 is shown attached to the BTE device 10 in FIG. 2. The ITE microphone earhook 22 comprises a second earhook 24, a microphone assembly 26, and a stalk 28 mechanically and electrically connecting the microphone assembly 26 to the earhook 24. The microphone assembly 26 includes a soundport 30 defined at a distal end of the microphone assembly 26. The stalk 28 preferably is bendable and preferably retains a position into which the stalk 28 is bent. In a preferred embodiment, the ITE microphone earhook 22 is attached to the BTE device 10 using the coaxial connector 20 of the '629 patent, however, those skilled in the art will recognize that a variety of apparatus and methods of attaching an ITE microphone to a BTE device are available. Further, the ITE microphone 25 need only be electrically connected 21 to the speech processor 23 of an ICS system, including a BTE system, and may include other means to secure the ITE microphone (e.g., any means that might be used to secure a common earphone may prove suitable to secure the ITE microphone) in place. These other means for connecting the ITE microphone to the BTE device are intended to come within the scope of the present invention.

Figure 3:
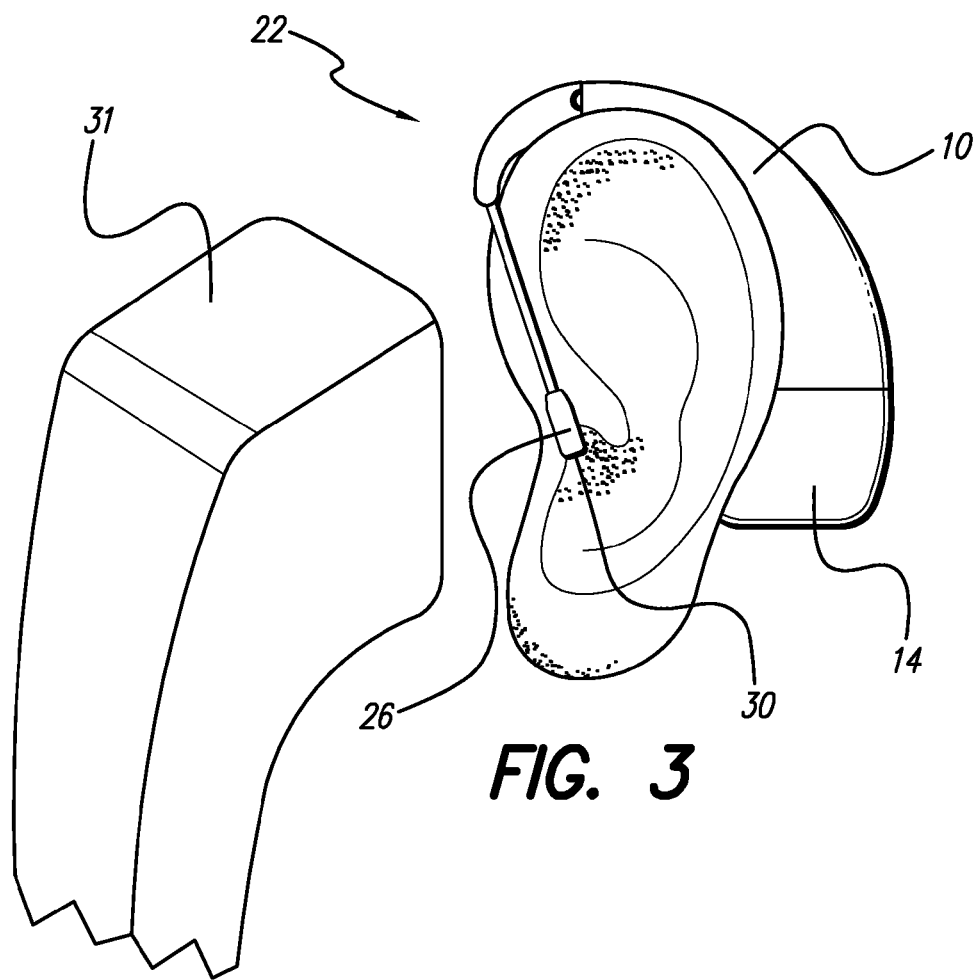
FIG. 3 depicts the BTE device with ITE microphone attached placed upon the ear of a user.

The ITE microphone earhook 22 and BTE device 10 are shown residing on the ear of a user in FIG. 3. The microphone assembly 26 preferably resides behind the tragus and directed towards the concha of the ear, with the soundport 30 facing downward and somewhat rearward. Some users may vary location of the microphone assembly 26, and these variations are intended to come within the scope of the present invention. The soundport 30 receives sound waves and is open to the volume between the earpiece 31 of a communications handset, such as a telephone handset, and the ear of a user.

Figure 4:
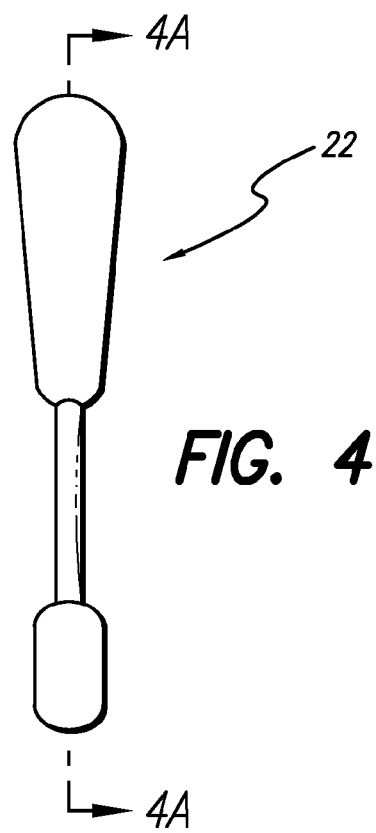
FIG. 4 shows a front view of the ITE microphone and earhook.
Figure 4A:
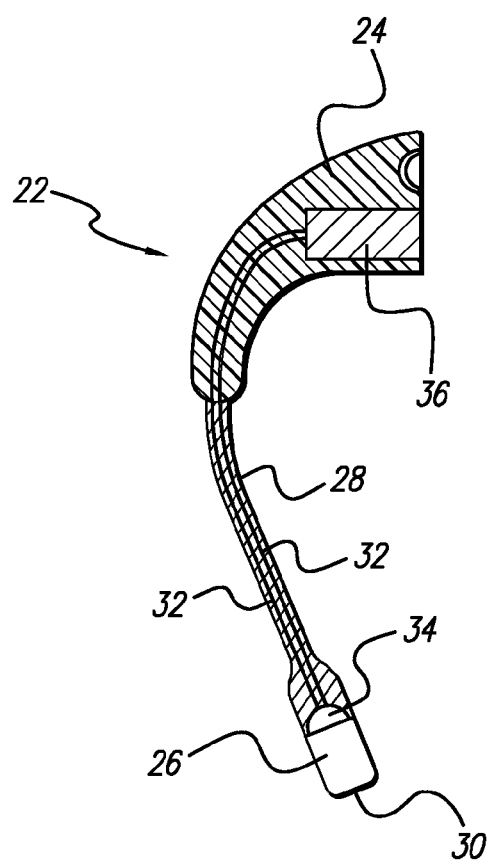
FIG. 4A shows a cross-sectional view of the ITE microphone and earhook taken along line 4A-4A of FIG. 4.

A front view of the ITE microphone earhook 22 is shown in FIG. 4, and a cross-sectional view of the ITE microphone earhook 22 taken along line 4A-4A of FIG. 4 is shown in FIG. 4A. A mating connector 36 is shown residing in the earhook 24. Such mating connector may be any connector suitable to electrically and mechanically connect the earhook 24 to the BTE device 10. Preferably, the mating connector 36 is the mating connector described in the '629 application. Those skilled in the art will recognize that other connectors may be used to connect the earhook 24 to the BTE device 10, including separate connectors for mechanical and electrical connecting. A microphone 34 resides in the microphone assembly 26, and is connected by at least one conductor 32 to the mating connector 36. While the conductor 32 preferably is electrically connected to the mating connector 36, in other embodiments the conductor 32 may be electrically connected to an electrical connector independent of the mating connector 36, or may exit the ITE microphone earhook 22 and electrically connect to a connector on the exterior of the BTE device 10.

Figure 5:
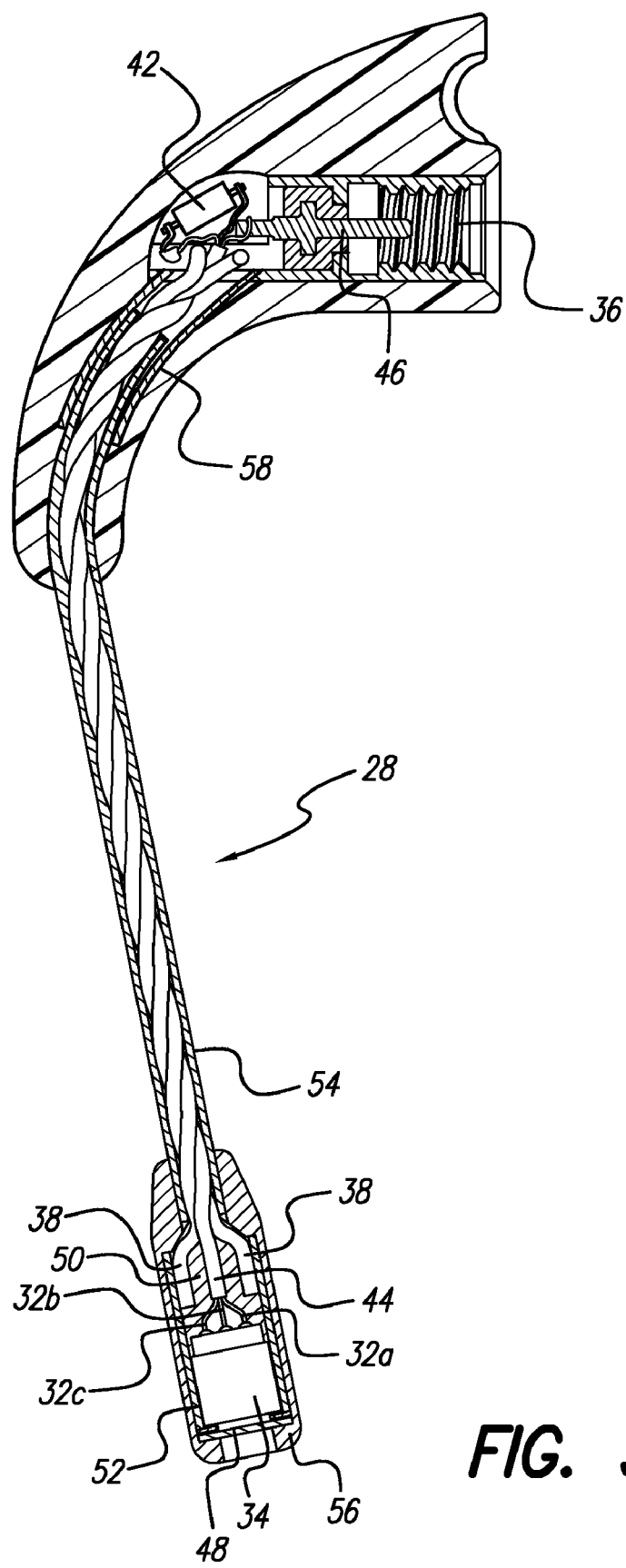
FIG. 5 shows a cross-sectional view of a preferred embodiment of the ITE microphone and earhook taken along line 4A-4A of FIG. 4.

A cross-sectional view of a preferred embodiment of the ITE microphone earhook 22, taken along line 4A-4A of FIG. 4, is shown in FIG. 5. The microphone 34 resides in a sleeve 52, wherein the sleeve 52 is preferably made from brass. A filter 48 seals the microphone 34 from the environment, while letting sound pass to the microphone 34. In a preferred embodiment, the microphone 34 comprises an FG Series microphone manufactured by Knowles Electronics Inc. in Itasca, Ill., and preferably an FG3329. The FG3329 microphone is operated in a two wire mode using a bias setting resistor 42. The at least one conductor 32 comprises three conductors 32a, 32b, and 32c attached at a distal end of the stalk 28 to three terminals on the FG3329 microphone. One of the three conductors 32a, 32b, and 32c is electrically connected to a contact 46 in the center of the mating connector 36, and two of the three conductors 32a, 32b, and 32c are connected to the bias setting resistor 42, and to the body of the mating connector 36. The three conductors 32a, 32b, and 32c are carried in a single cable 44, and the cable 44 is wound with two stiffening members 38, which stiffening members 38 are preferably made from wire, more preferably from zinc or copper. The stiffening members 38 enable the stalk 28 to be bent into a desired shape, and to retain the shape. The wound combination of the cable 44 and the stiffening members 38 is covered by shrink tubing 54. The stiffening members 38 allow the stalk 28 to be bent into various shapes to better fit a user, and to retain such shapes. The stiffening members 38 are connected to the sleeve 52. The stiffening members 38 provide the stalk 28 with the ability to be bent and to retain the position into which the stalk 28 is bent. The volume 50 behind the microphone 34 is filled with potting compound to prevent the conductors 32a, 32b, and 32c from flexing and detaching from the microphone 34 when the stalk 28 is adjusted. The entire assembly including the microphone 34, sleeve 52, and conductors 32a, 32b, and 32c, is covered by a boot 56, preferably molded from an elastomer.

A method of constructing the ITE microphone earhook 22 is as follows. The conductors 32a, 32b, and 32c are soldered to terminals on the microphone 34 to form a first sub-assembly. The stiffening members 38 are soldered to the sleeve 52 to form a second sub-assembly. The first sub-assembly is inserted into the second sub-assembly, wherein the conductors 32a, 32b, and 32c are guided into the end of the sleeve 52 opposite the stiffening members 38, until the end of the microphone 34 opposite the conductors 32a, 32b, and 32c is flush with the end of the sleeve 52 opposite the stiffening members 38. The resulting cavity in the sleeve 52 containing the conductors 32a, 32b, and 32c is filled with potting compound and allowed to cure. (This creates a solid structure of the microphone, cable, sleeve and flexible members so that any bending in the stalk will not be transferred to the solder joints of the conductors 32a, 32b, and 32c that would weaken and eventually fail the connection.) After curing of the potting compound, the stiffening members 38 and the cable 44 are twisted together as a group to about 3 turns per inch. Shrink tubing 54 is applied over the stiffening members 38 and the cable 44, up to the base of the sleeve 52, to form the ITE microphone stalk 28. The filter 48 is attached to the end of the sleeve 52 opposite the stalk 28 to protect the microphone 34 from moisture. The microphone 34 and stalk 28 assembly is then inserted, stalk 28 first, through the large opening of the microphone boot 56. The microphone boot 56 will stretch over the sleeve 52 and encapsulate the entire microphone assembly. The curved tube 58 is soldered to the mating connector 36, and the stalk 28 is inserted into the curved tube 58. The proper length of the stalk 28 is determined, and the two stiffening members 38 are then soldered to the inside diameter of the mating connector 36 for a mechanical connection. The conductors 32a, 32b, and 32c are then soldered to the appropriate terminals of the mating connector 36 and the resistor 42. After soldering is completed, the volume around the soldered connections is potted with epoxy to cover the connections and the resistor 42 to protect them from damage during the over mold process of the ear hook. The mating connector 36, curved tube 58, and adjacent end of the stalk 28 are over molded with a medical grade PVC to form the ear hook to complete the ITE microphone earhook 22.

An ITE microphone for use with BTE ICS systems has been described. The ITE microphone resides within a sealed chamber formed by the telephone, or other communications device, handset earpiece, and the ear. As a result of sealing in the sound waves, the low frequency near field acoustic degradation otherwise experienced by the user are substantially mitigated, and a significant improvement in the quality of the sound perceived by the ICS system user results. The ITE microphone performs equally well with traditional telephones and with low magnetic field phones and cell phones using piezo transducers which do not couple well with telecoils.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for use with a Behind The Ear (BTE) Implantable Cochlear Stimulation (ICS) system, the BTE including a removable earhook and the ICS system including a speech processor, the apparatus comprising:
   a microphone assembly, wherein the microphone assembly includes a microphone which converts audio sounds into electrical signals which are processed by the speech processor to generate signals provided to an implantable circuit adapted to generate electrical pulses to stimulate nerves in the cochlea;
   means for positioning the microphone assembly to receive sound waves through a port, wherein the sound waves are directed from a volume between a user's ear and the earpiece of a communications handset held to the ear; and
   means for electrically connecting the microphone to the speech processor,
   wherein the positioning means includes a first end attached to the earhook and a second end directed towards the inside of a user's ear,
   wherein the microphone assembly is attached to the second end of the positioning means.

2. The apparatus of claim 1 wherein the communications handset is a telephone handset.

3. The apparatus of claim 1 wherein the positioning means comprises a stalk adapted to connect the microphone assembly to the earhook.

4. The apparatus of claim 3 wherein the stalk is adapted to be bendable and to retain the bend once bent, thereby adjusting the position of the microphone assembly.

5. The apparatus of claim 4 wherein the stalk is formed of shrink tubing.

6. The apparatus of claim 1 wherein the earhook is removably attachable to a coaxial connector, wherein the coaxial connector is attached to a case of the speech processor.

7. The apparatus of claim 1 further including a filter at a distal end of the microphone assembly, wherein the filter seals the microphone from the environment.

8. The apparatus of claim 7 wherein the microphone assembly further includes a sleeve and wherein the microphone resides in the sleeve.

9. The apparatus of claim 8 wherein the microphone, the sleeve, and the electrical connecting means are covered by a boot, wherein the boot includes an access hole for the port.

10. The apparatus of claim 9 wherein the boot is molded from an elastomer.

11. An apparatus for use with a Behind The Ear Implantable Cochlear Stimulation system, comprising:
    an earhook configured to be removably attachable to a Behind The Ear (BTE) unit of an Implantable Cochlear Stimulation (ICS) system;
    a microphone assembly, wherein the microphone assembly includes a microphone which converts audio sounds into electrical signals which are processed by the speech processor to generate signals provided to an implantable circuit adapted to generate electrical pulses to stimulate nerves in the cochlea;
    means for positioning the microphone assembly to receive sound waves through a soundport, wherein the sound waves are directed from a volume between a user's ear and the earpiece of a communications handset held to the ear; and
    means for electrically connecting the microphone to the speech processor,
    wherein the means for positioning includes a first end attached to the earhook and a second end attached to the microphone, and wherein the microphone is adjusted to reside within the space defined by a concha of a user's ear with the soundport directed downward when the BTE unit is worn on the user's ear.

12. The apparatus of claim 11 wherein the microphone assembly is adjusted so that when an earpiece of a communications handset is held to the ear, the soundport is open to the volume between the earpiece and the user's ear.

13. The apparatus of claim 12 wherein the communications handset is a telephone handset.

14. The apparatus of claim 11 wherein the means for positioning comprises a stalk adapted to connect the microphone assembly to the earhook.

15. The apparatus of claim 14 wherein the stalk is adapted to be bendable and to retain the bend once bent, thereby adjusting the position of the microphone assembly.

16. The apparatus of claim 15 wherein the stalk is formed of shrink tubing.

17. The apparatus of claim 11 wherein the earhook is removably attachable to a coaxial connector, wherein the coaxial connector is attached to a case of the speech processor.

18. The apparatus of claim 11 further including a filter at a distal end of the microphone assembly, wherein the filter seals the microphone from the environment.

19. The apparatus of claim 18 wherein the microphone assembly further includes a sleeve and wherein the microphone resides in the sleeve.

20. The apparatus of claim 19 wherein the microphone, the sleeve, and the electrical connecting means are covered by a boot, wherein the boot includes an access hole for the soundport.

* * * * *